United States Patent [19]

Arold et al.

[11] 4,337,359
[45] Jun. 29, 1982

[54] PREPARATION OF DIMETHYL POLYSULPHIDES

[75] Inventors: Hermann Arold, Wuppertal; Siegbert Humburger, Leverkusen; Hans-Joachim Diehr, Wuppertal; Helmut Porkert, Baytown, all of Fed. Rep. of Germany

[73] Assignee: Bayer Aktiengesellschaft, Leverkusen, Fed. Rep. of Germany

[21] Appl. No.: 249,241

[22] Filed: Mar. 30, 1981

[30] Foreign Application Priority Data

Apr. 5, 1980 [DE] Fed. Rep. of Germany ....... 3013396

[51] Int. Cl.³ .......................................... C07C 148/00
[52] U.S. Cl. ........................................ 568/21; 568/18
[58] Field of Search .................................. 568/21, 18

[56] References Cited

U.S. PATENT DOCUMENTS

| 3,103,465 | 9/1963 | Goodhue et al. | 568/21 |
| 3,367,975 | 2/1968 | Liggett | 568/21 |
| 3,376,313 | 4/1968 | Wallace | 568/21 |
| 3,444,241 | 5/1969 | Eisfeid et al. | 568/21 |

FOREIGN PATENT DOCUMENTS

| 46-37499 | 11/1971 | Japan | 568/21 |
| 380645 | 3/1971 | U.S.S.R. | 568/21 |

OTHER PUBLICATIONS

Hilgetag et al., Chem. Abst. 19848c vol. 53, 1959.
Hilgetag et al., Chem. Abst. 21748 vol. 53, 1959.

Primary Examiner—Jane T. Fan
Attorney, Agent, or Firm—Sprung, Horn, Kramer & Woods

[57] ABSTRACT

A process for the preparation of a dimethyl polysulphide of the formula $$CH_3-S_x-CH_3$$

in which
x is at least 1, comprising reacting a polysulphide of the formula $$M_yS_x$$

in which
M represents an alkali metal atom or alkaline earth metal atom, and
y is 1 or 2, with O,O,O-trimethyl thiophosphate of the formula $$(CH_3O)_3P=S.$$

10 Claims, No Drawings

PREPARATION OF DIMETHYL POLYSULPHIDES

The present invention relates to an unobvious process, which is simple to carry out industrially, for the preparation of certain known dimethyl polysulphides by methylation of alkali metal sulphides or alkaline earth metal sulphides with O,O,O-trimethyl thiophosphate.

In industrial processes for the preparation of O-methyl-thiophosphoric acid chlorides, which are used as intermediates for plant protection agents, relatively large amounts of O,O,O-trimethyl thiophosphate are unavoidably obtained. The removal of this compound can present an ecological problem, and in addition is associated with high costs. It is thus of great interest to put O,O,O-trimethyl thiophosphate to an appropriate use.

The present invention now provides a process for the preparation of dimethyl polysulphides of the general formula $$CH_3-S_x-CH_3 \quad (I)$$

in which x denotes an integer or a fraction, preferably from 2 to 5, in which a polysulphide of the general formula $$M_yS_x \quad (II)$$

in which
M represents an alkali metal atom or alkaline earth metal atom (preferably sodium, potassium or calcium, more preferably sodium or potassium and, especially sodium),
y is 1 or 2 and
x have the abovementioned meaning, is reacted with O,O,O-trimethyl thiophosphate of the formula $$(CH_3O)_3P=S \quad (III)$$

and the polysulphides of formula (I) are isolated, or isolated and purified as desired, with the optional isolation of the phosphoric acid methyl ester salts also formed, for further use.

If, for example, sodium polysulphide of the formula $Na_2S_{3.5}$ and O,O,O-trimethyl thiophosphate are used, the cource of the reaction according to the present invention is illustrated by the following equation:

$$Na_2S_{3.5} + (CH_3O)_3P=S \xrightarrow{90°C.}$$

$$CH_3S_{3.5}CH_3 + CH_3O-\overset{O}{\underset{S}{\overset{\|}{P}}}\diagdown Na_2$$

The O,O,O-trimethyl thiophosphate of the formula (III) which can be used, according to the invention, as the starting material is a known compound, as are the polysulphides of the formula (II), which (depending on the desired end product) can be employed as the monosulphide, disulphide, trisulphide, tetrasulphide, pentasulphide and so on or as mixtures of these sulphides, integers resulting for single compounds of the formula (II) (or I) and fractions resulting, as average values, in the case of mixtures. In the polysulphides of the formula (II), M preferably represents potassium or, especially, sodium.

The molar ratios of the starting compounds can vary within a wide range in carrying out the process according to the invention. Preferably, 1 mole of O,O,O-trimethyl thiophosphate of the formula (III) is reacted with about 0.5 to 3 moles, especially about 1 to 2 moles, of polysulphide of the formula (II).

The reaction is in general allowed to proceed under normal pressure.

The reaction is preferably carried out at a temperature between about 10° C. and 200° C., especially about 20° C. to 100° C., and in a particular preferred embodiment of the invention, at a temperature of about 75° C. to 95° C.

The reaction can be carried out in water, in mixtures of organic solvents and water or in organic solvents, preferably in water or in the presence of water. In the case of mixtures of water and organic solvents, the mixing proportions for the process according to the invention can be varied over wide ranges. Thus, for example, the volumetric ratio of water to organic solvent can be between about 1:100 and 100:1, preferably between about 1:10 to 10:1.

Possible organic solvents are, above all, polar solvents, such as alcohols (for example, ethanol, n- and i-propanol and n-butanol and, preferably, methanol), ketones (for example methyl isobutyl ketone), cyclic ethers (for example dioxane and tetrahydrofuran), and lower dialkylformamides (for example dimethylformamide). Organic polar solvents which are water-miscible are preferred. The use of water or methanol or mixtures of water and methanol in any desired mixing proportions is very particularly preferred.

The reaction mixture is worked up by the generally customary methods. If the process according to the invention is carried out in water, the polysulphides of the formula (I) which have formed and have separated out (and which are sparingly soluble in water) can easily be separated off by the customary methods. If water mixed with an organic solvent is used as the solvent, water must be added, where necessary, when the reaction has ended, in an amount such that the polysulphide separates out. An analogous procedure must be followed if a water-miscible organic solvent is employed, without the addition of water. If a water-immiscible organic solvent is used, the water-soluble by-products can be removed by washing the reaction mixture when the reaction has ended. The polysulphides of the formula (I) can be further reacted directly, in the organic solution, or they can be isolated from the solution by customary methods (for example by distilling off the solvent). The polysulphides prepared according to the invention have a high purity, so that purification (for example by distillation) is not required for most applications.

When water or mixtures of water and organic solvents are used as the solvent, the readily water-soluble phosphoric acid methyl ester salts formed in the reaction are present in the aqueous phase. If non-aqueous solvents are used, the phosphoric acid methyl ester salts are in the wash water with which, in this case, the reaction mixture is expediently washed after the reaction. They can be further used, for example as intermediate products for plant protection agents, in aqueous solution, or directly, or after being isolated. If such a use is not desired, they can be removed as waste substances in a considerably simpler manner than the trimethyl thiophosphate starting material.

In a particular embodiment, the process according to the invention can also be carried out in the customary manner as a multi-stage process in a cascade arrangement or continuously.

The dimethyl polysulphides which can be prepared by the process according to the invention are obtained in a very high purity. They are valuable intermediate products, for example for the preparation of known methylthiophenols, which in turn are used, for example, as intermediate products for plant protection agents.

It should also be mentioned here that other dialkyl polysulphides, for example diethyl polysulphide, can in principle also be obtained by the process according to the invention.

The procedure for the process according to the invention is to be illustrated in the following examples:

EXAMPLE 1

312 g (2 moles) of O,O,O-trimethyl thiophosphate were added to 943 g of a 45% strength (percent by weight) solution of sodium polysulphide of the composition $Na_2S_{3.5}$ (2.6 moles) at 85° C. to 90° C. in the course of 2 hours, while stirring. After the addition, the reaction mixture was stirred at 90° C. for a further 5 hours. The batch was then cooled to 20° C. and 280 g (1.97 moles) of dimethyl polysulphide were separated off as the organic phase.

The following table, in which the essential reaction conditions are given, contains further examples:

We claim:

1. A process for the preparation of a dimethyl polysulphide of the formula $$CH_3-S_x-CH_3$$

in which x is from 1 to 5, comprising reacting a polysulphide of the formula $$M_yS_x$$

in which
M represents an alkali metal atom or alkaline earth metal atom, and
y is 1 or 2,
with O,O,O-trimethyl thiophosphate of the formula $$(CH_3O)_3P=S.$$

2. A process according to claim 1, wherein the reaction is carried out at a temperature between about 10° and 200° C.

3. A process according to claim 1, wherein the reaction is carried out at a temperature between about 20° and 100° C.

4. A process according to claim 1, wherein the reaction is carried out at a temperature between about 75° and 95° C.

5. A process according to claim 1, in which M is sodium and y is 2.

6. A process according to claim 1, in which x is from about 2 to 5.

TABLE

| Example | O,O,O-Trimethyl-thiophosphate, g | Polysulphide g | Polysulphide formula | Solvent | Reaction time, hrs. | Reaction temperature °C. | Dimethyl-polysulphide g |
| --- | --- | --- | --- | --- | --- | --- | --- |
| 2 | 156 | 99 | $Na_2S_{3.5}$ | $H_2O$/Methanol (3:1)* | 12 | 25 | 70 |
| 3 | 156 | 99 | $Na_2S_{3.5}$ | $H_2O$/Methanol (3:1)* | 8 | 50 | 72 |
| 4 | 156 | 197.5 | $Na_2S_{3.5}$ | $H_2O$ | 8 | 60 | 135 |
| 5 | 156 | 197.5 | $Na_2S_{3.5}$ | $H_2O$ | 7 | 90 | 140 |
| 6 | 156 | 202.5 | $CaS_{3.5}$ | $H_2O$ | 8 | 90 | 138 |
| 7 | 156 | 197.5 | $Na_2S_{3.5}$ | Methanol | 8 | 60 | 135 |

*parts by volume

It will be understood that the specification and examples are illustrative but not limitative of the present invention and that other embodiments within the spirit and scope of the invention will suggest themselves to those skilled in the art.

7. A process according to claim 1, in which water is used as a solvent.

8. A process according to claim 1, in which methanol is used as a solvent.

9. A process according to claim 1, in which a solution of water and methanol is used as a solvent.

10. A process according to claim 4, in which M is sodium, y is 2, x is from about 2 to 5 and at least one of water and methanol is used as a solvent.

* * * * *